United States Patent [19]

Hepburn

[11] Patent Number: 4,538,600
[45] Date of Patent: Sep. 3, 1985

[54] ADJUSTABLE SPLINT

[75] Inventor: George R. Hepburn, Severna Park, Md.

[73] Assignee: Dynasplint Systems, Inc., Baltimore, Md.

[21] Appl. No.: 545,848

[22] Filed: Oct. 27, 1983

[51] Int. Cl.³ ............................................. A61F 5/04
[52] U.S. Cl. ........................................ 128/88; 128/77
[58] Field of Search .................... 128/88, 80 F, 80 C, 128/87 R, 83, 85, 77, 78

[56] References Cited

U.S. PATENT DOCUMENTS 4,237,873 12/1980 Terry ..................................... 128/77
4,397,308 8/1983 Hepburn ............................... 128/88

Primary Examiner—John D. Yasko
Assistant Examiner—Christa K. Scott
Attorney, Agent, or Firm—Larson and Taylor

[57] ABSTRACT

An adjustable splint assembly comprising a lower strut and an upper strut pivotably connected to said lower struct, one of said struts having at one end a pivotably mounted head portion defining a cam surface, an adjustable biasing means mounted within the other strut and biased into engagement with said cam surface, for applying a quantifiable force tending to align or approximate said upper and lower struts and means for securing said splint assembly to a limb.

16 Claims, 9 Drawing Figures

ADJUSTABLE SPLINT

BACKGROUND OF THE INVENTION

Field of the Invention

This invention relates to an adjustable splint. More particularly, this invention relates to an adjustable splint useful in treating impairments in body joints such as wrists, and the like from flexion contracture, weakness in the supporting musculature, or some other malady inhibiting the integrity of the body joint in accomplishing extension.

People often develop flexion contractures in wrists and other joints from many and various causes. Weakness, disuse, fractures, surgeries, traumatic injuries, illness and other causes have been known to cause loss of ability to extend the body joint otherwise known as a flexion contracture. No device presently exists to reduce flexion contractures by adjustable, quantifiable pressure as does the adjustable splint for extension as described herein.

Many splint devices and mechanisms have been designed to be influential at the knee either for support or for mobilizing the knee joint. Illustrative of such devices are those described in U.S. Pat. Nos. 3,055,359; 3,928,872; 3,785,372 and 3,799,159. However, all of these devices are not designed to reduce wrist flexion contractures and cannot be tolerated by the patient population for a long enough period to effectively reduce a contracture. Moreover, none of the devices offer a satisfactory means for adjusting the pressure exerted by the lateral struts of the splint devices.

OBJECTS OF THE INVENTION

Accordingly, it is an object of the invention to provide an improved splint device for reducing flexion contractures about a wrist.

Yet another object of the invention is to provide a splint device, which allows easy gradual adjustment to the quantifiable force desired on an extremity acting across a body joint.

A further object of the invention is to provide a splint device for incarcerated patients to help obtain a higher level of independence in their activities of daily living, self care and ambulatory activities.

A further object would be to provide an improved splint for providing support to a wrist in cases where muscular weakness exists.

SUMMARY OF THE INVENTION

These and other objects of the invention are obtained by an adjustable splint assembly comprising a lower strut and an upper strut pivotably connected to said lower strut, one of said struts having at one end a pivotably mounted head portion defining a cam surface, an adjustable biasing means mounted within the other strut and biased into engagement with said cam surface, for applying a quantifiable force tending to approximate or align said upper and lower struts, a palmer pressure pad, means for adjusting the splint assembly to the palm, and means for securing said splint assembly to the forearm.

In a preferred embodiment the present invention comprises a pair of lower struts and a pair of upper struts, each member of the pair of upper struts, said members of each pair being spaced apart a distance to accomodate limb parts distal and proximal to the limb joint, at least one of said struts having at one end, a pivotably mounted head portion defining a cam surface, an adjustable biasing means mounted within the strut pivotably connected to said cam surface-containing strut and biased into engagement with said cam surface, for applying a quantifiable force tending to align or approximate the cam surface-containing strut with the adjustable biasing means containing strut and means provided said pair of upper struts and said pair of lower struts for securely holding therebetween said distal and proximal parts of a limb.

The means for adjusting the splint assembly to the palmer pressure pad comprises means attached to said palmer pressure pad providing both rotational and vertical adjustment of said palmer pressure pad and means connecting the palmer pressure pad to the end of the lower or distal strut, said connecting means containing at least one lateral adjusting bar for medial and lateral adjustment of said polymer pressure pad.

In a preferred embodiment the means attached to said palmer pressure pad providing said rotational and vertical adjustment thereof comprises a base plate having an arcuate slot, a member fixed to said pad and projecting through said slot about which the pad rotates and a means slidably mounted thereto for vertical adjustment of said pad, said slideably mounted means containing means for receiving said bar for medial and lateral adjustment of said pad.

Advantageously a pair of lower, i.e. distal, struts and a pair of upper, i.e. proximal struts are employed in which case the ends of the distal struts are provided with suitable interconnecting means to which the means containing the lateral adjusting bars are connected.

BRIEF DESCRIPTION OF THE DRAWINGS

The invention will appear more clearly from the following detailed description when taken in connection with the following drawings which show by way of example a preferred embodiment of the invention.

In the drawings.

DESCRIPTION OF THE PREFERRED EMBODIMENT

Figure 1:
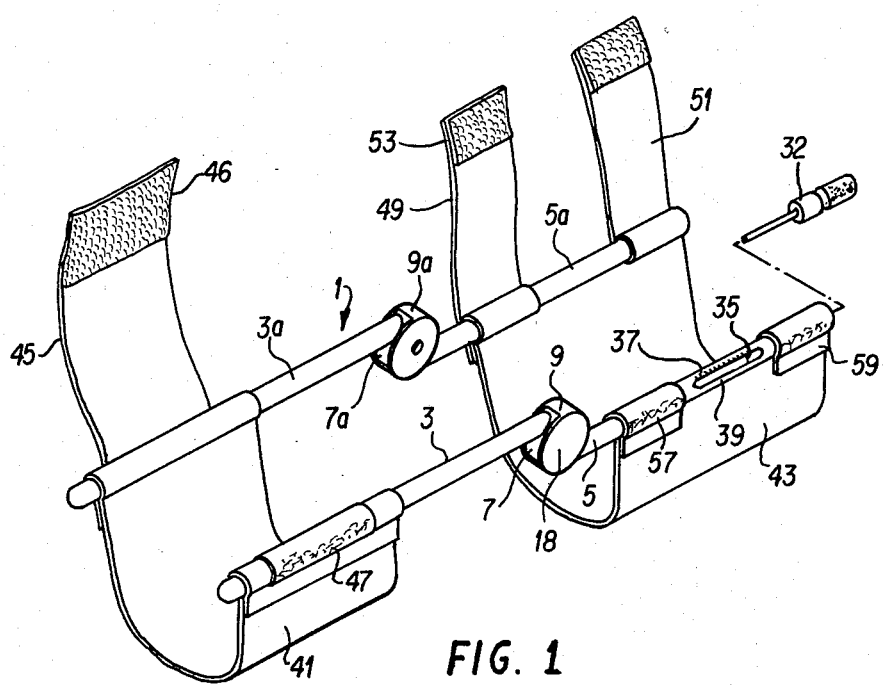
FIG. 1 is a perspective view of the adjustable splint for reducing flexion contractures.
Figure 2:
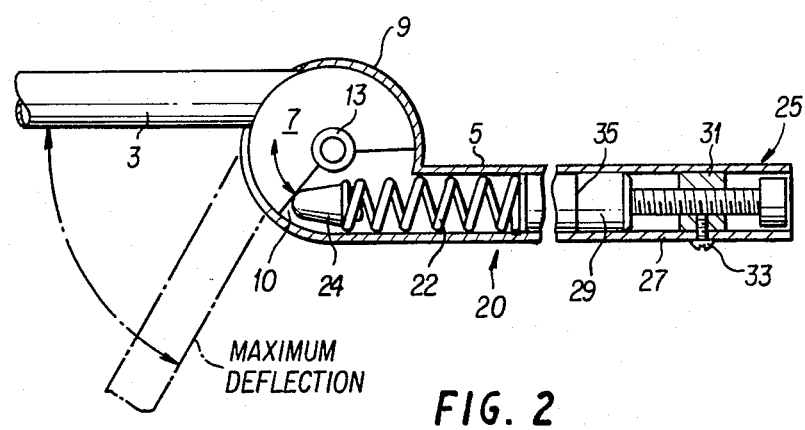
FIG. 2 is a perspective view of one upper and one lower strut assembly of the adjustable splint of the invention for reducing flexion contractures wherein a strut is broken away to show the adjustable spring-loaded means mounted therein.
Figure 3:
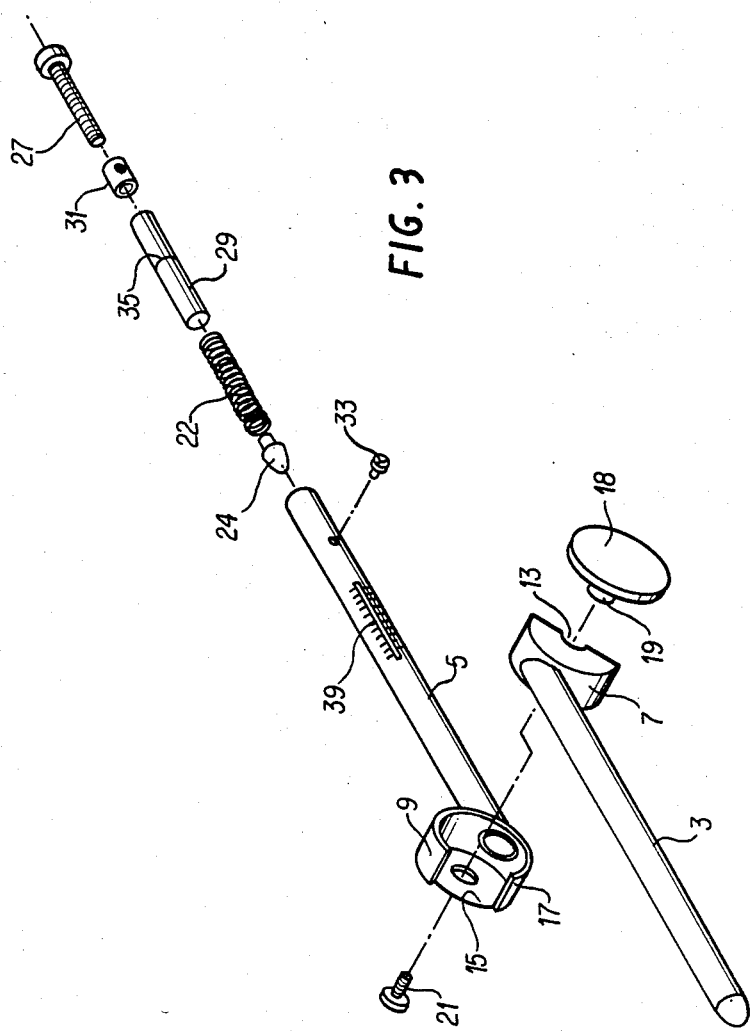
FIG. 3 is a perspective, exploded view of the splint device of FIG. 1.

Referring to FIGS. 1–3, an adjustable splint device 1 is comprised of lower struts 3 and 3a and upper struts 5 and 5a. Lower strut 3 contains a rounded head portion 7 and upper strut 5 contains a socket head portion 9 which receives head portion 7 for pivotable engagement therewith. Rounded head portion 7 is cut away to define a cam surface 10 and is provided with an axial surface recess 13. A first surface plate 15 having a screw hole 17 covers one side of the combined head portions 7–9 and a second plate member 18 having a threaded protruding member 19 (see FIG. 3) covers the other half of the combined head portion 7–9. When surface plate member 18 is positioned over the combined head portion 7–9 protruding member 19 projects through the axial circular recess 13 and receives a screw 21 through screw hole 17. Lower strut 3a and upper strut 5a are similarly pivotably connected by corresponding members bearing like numbers but carrying the distinguishing suffix "a".

Figure 7:
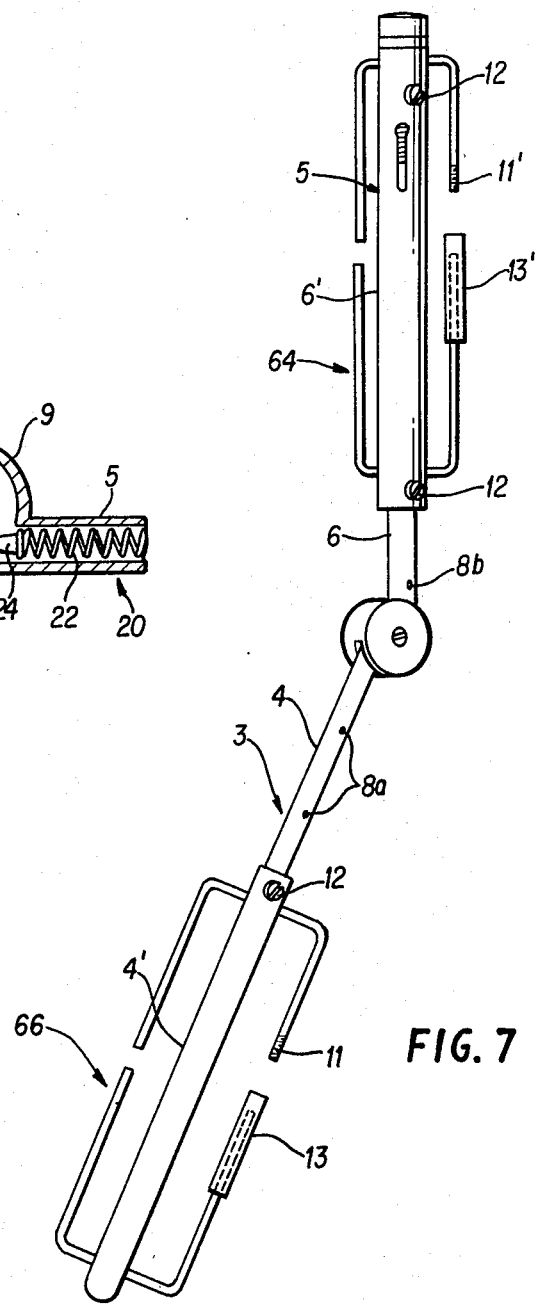
FIG. 7 is a perspective view of the splint device provided with a telescoping slidable adjustable wire assembly for mounting of the means by which the device is secured to the limb.

The lower and upper struts may be constructed of any material of sufficient strength such as plastic, metal, wood and the like. Particularly preferred are struts made of stinless steel metal. At least one of the struts should be at least partially hollow so as to house therein the adjustable spring mechanism of the invention. Most advantageously, all of the struts are tubular in construction so as to provide a lightweight product. Preferably each of the struts 3, 3a, 5 and 5a can be comprised of two telescoping portions as shown in the single strut depicted in FIG. 7 so as to permit lengthening and shortening of the struts. Directing attention to FIG. 7, strut 3 is comprised of telescoping portions 4 and 4', strut 5 of telescoping portions 6 and 6'. The inner portions 4 and 6 are provided with a series of threaded holes 8 and 8a and the outer portions 4' and 6' with holes and threaded holes, respectively, through which screws 12 pass for threaded engagement with a coincident hole 8 and 8a. Where the distal strut is of larger diameter than the proximal strut as shown in FIG. 7 it is preferable to provide threads in the holes of the outer portion 6'. Such a telescoping feature provides a splint which can be adjusted to several different lengths allowing the splint to fit a greater number of individuals. It should be understood that in this embodiment the splint device combination of the invention will include a series of spring abutting members 20 (see FIG. 3) of varying lengths so as to accomodate different limb lengths.

The adjustable spring-loaded mechanism designated generally as 20 may be provided in either the lower or the upper struts. Preferably, only the lower struts 5 and 5a are provided with the adjustable spring mechanism.

Figure 6:
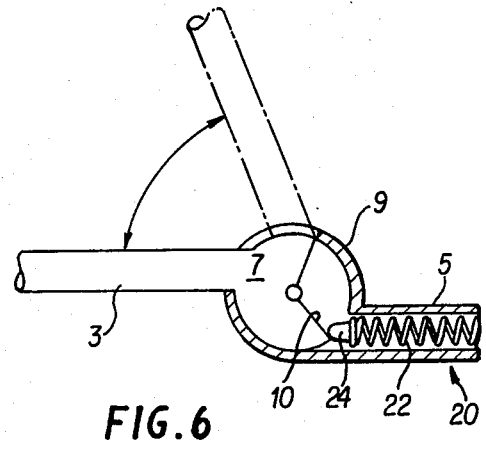
FIG. 6 is a perspective view of one upper and one lower strut assembly of the adjustable splint of the invention for reducing extension contractures wherein a strut is broken away to show the adjustable spring-loaded means mounted therein.

The adjustable spring mechanism 20 is comprised of a spring 22 to which is attached a nose element 24 that bears on cam surface 10. Coil or clock springs are generally preferred but in some instances leaf springs are advantageously employed. An adjustable screw means indicated generally as 25 abuts the other end of the spring 22 and produces a quantifiable force which tends to either extend, (i.e. align the lower strut 5 with the upper strut 3 and lower strut 5a with upper strut 3a in a parallel fashion) as shown in FIG. 2 or to approximate (i.e. bring together the lower strut 5 with the upper strut 3 and lower strut 5a with upper strut 3a) as shown in FIG. 6. As maximum flexion is approached, tension is created in the compression coiled spring 22. The adjustable screw means 25 is comprised of an "Allen" head screw or slotted head screw 27 threaded to a spring-abutting member 29. The "Allen" head screw is fixed within upper strut 3 by screw 33. The "Allen" head screw 27 receives and is turned by an "Allen" socket wrench 32 (see FIG. 1) whereas a slotted head screw is adjustable with a conventional screwdriver blade. The turning of the screw creates greater compression of spring 22 thereby exerting greater force on the cam surface 10 of the lower strut 5 to exert a one way tension. The tension capability of the spring mechanism can range from 0 pounds tension up to the maximum tension capable of the spring. In general, the tension of the spring mechanism will range from 0 pounds tension up to 5 pounds of tension and the tension exerted by the spring can be varied at any point of joint range of motion, say from 20° flexion to 70° extension of the joint.

Whereas the specific joint range of motion to which tension can be exerted is preferred to be 20° flexion through 70° extension for reducing flexion contractures in the wrist, the joint range of motion at which tension can be applied can vary to nearly any degree in the 360° circular range simply by varying the point of attachment of the inner portion of strut 3 to rounded head portion 7 and by varying the point of attachment of the inner portion of strut 5 to socket head portion 9. Likewise, the same variations apply to struts 3a and 5a.

The purpose of varying the point in the joint range to which tension is applied is obvious when you consider that different illnesses and injuries cause different types of limitations at different degrees of joint ranges of motion thereby making necessary different points in the joint range at which tension must be applied to improve their condition. The spring mechanism can be calibrated to exert the desired range of tension. The calibration can be effected by providing spring-abutting member 29 with a poundage indicator line 35 and a calibration scale 37 about the lower strut 5 which scale has a slot 39 through which the poundage indicator 35 is visible.

While the preferred adjustable biasing means of the invention is a spring means such as described, equivalent biasing means such as air or hydraulic powered biasing means will readily come to the mind of those skilled in this art.

Any suitable means can be utilized to secure pivotably mounted struts 3 and 5 and pivotably mounted struts 3a and 5a to the limb so that they lie lateral to the joint with the axis of rotation coinciding as closely as possible to the axis of rotation of the joint. As shown in the figures, the securing means comprise a proximal cuff 41 attached to and extending between upper strut 3a and upper strut 3 and distal cuff 43 attached to and extending between lower strut 5a and lower strut 5. The length of the proximal cuff 41 and distal cuff 43 is of sufficient distance to comfortably accomodate the limb parts distal and proximal to the limb joint. An overlying flap 45 is attached at one end to upper strut 3a and contains on its outer surface an attaching means such as velcro hooks 46 by which the flap can wrap about the proximal portion of the limb and be secured to the velcro loops 47 on the outer surface of the proximal cuff wrapped about upper strut 3. Distal cuff 43 is secured to lower strut 5a and 5 and contains two separate flaps 49 and 51 each containing on their outside velcro attaching loops 53 and 55 respectively. The flaps 49 and 51 are of sufficient length to extend over and secure the limb portion lying in distal cuff 43 by attachment to the velcro loops receiving areas 57 and 59 provided on the distal cuff 43 about the lower strut 5.

It should be understood that a single combined strut, such as upper strut 3 pivotably connected to lower strut 5, can alone be utilized as a splint device by securing same by suitable means to the lateral side of the limb to be treated. Again, any suitable means for strapping or securing the splint device of the invention can be used, for example, by distal and proximal cuffs of sufficient lengths to wrap around the distal and proximal portions of the limb being treated. The straps 45, 49 and 51 as well as the cuffs 41 and 43 can be secured to the struts in any suitable manner as by sewing, typing, etc.

Figure 4:
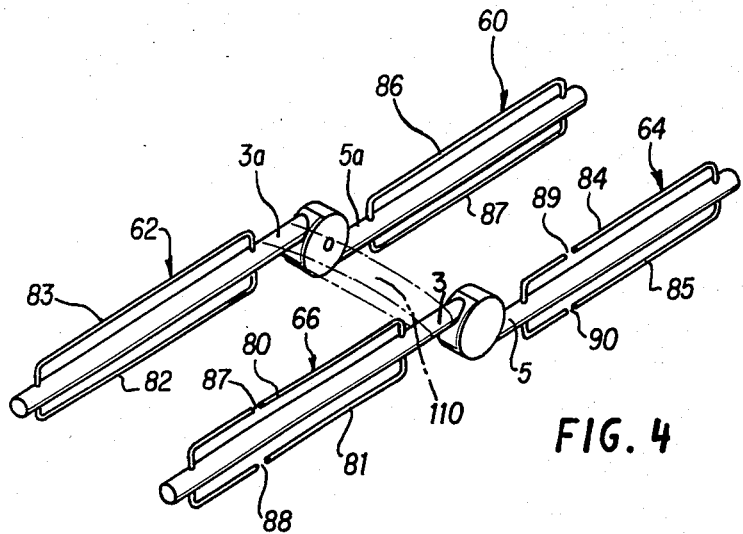
FIG. 4 is a perspective view of the splint device provided with a "break apart" wire assembly for mounting of the means by which the device is secured to the limb.

To facilitate the attachment of the cuffs and straps, however, it is preferred that wire assemblies, designated generally in FIG. 4 as 60, 62, 64 and 66, be fastened as by welding to struts 5, 5a and 3 and 3a, respectively. The wire assembly 62 is comprised of an upper thin wire portion 83 and a thin wire lower portion 82, each of which wire assembly portions extend from one end of strut 3a to the other. Similarly, wire assembly 60 is comprised of an upper thin wire portion 86 and a lower wire portion 87. In the preferred embodiment shown in FIG. 7 the shorter sides of the wire assemblies are of continuous construction and bent for more secure attachment as by welding to the struts. In the embodiment of FIG. 4 wire assemblies 64 and 66 differ from wire assemblies 60 and 62 in being of the "break apart" type as will be explained below so as to facilitate insertion and removal of the cuffs or straps for cleaning, replacing, etc. Thus, wire assembly 66 is comprised of an upper thin wire portion 80 and a lower thin wire portion 81 both of which are broken at 87 and 88, respectively, so that the wire can be pulled apart slightly when the cuff are to be attached or removed. Similarly, wire assembly 64 is comprised of a thin upper wire section 84 and a thin lower wire section 85 both of which are broken at 89 and 90, respectively. In the embodiment of FIG. 7, however, all of the wire assemblies are of "break apart" type but one, wire portion on both the distal and proximal struts, that is, two of the four receiving wires contains telescoping sections B and B'. Telescoping sections B and B' are internally threaded at one end for engagement with threaded end 11 and 11' or the wire portion. This gives the wire fixture added strength. Normally a wire assembly with telescoping sections B and B', however, is only used on the side of the strut which makes an angle of 65° when flexed.

When the adjustable splint is to be used for extension of a joint, a strap 110 is provided between struts 3 and 3a as shown in FIG. 4 and between 5 and 5a. Use of a strap 110 both between struts 3 and 3a and 5 and 5a is often advisable in many instances particularly in reducing knee flexion contractures. Strap 110 in these applications is important in order to maintain optimal alignment of the upper and lower struts along the parallel of the limb part proximal and distal to the joint. Strap 110 also helps maintain the axis of rotation of the splint joint assembly more coincident with the axis of rotation of the body joint to which the splint is being applied.

Figure 5:
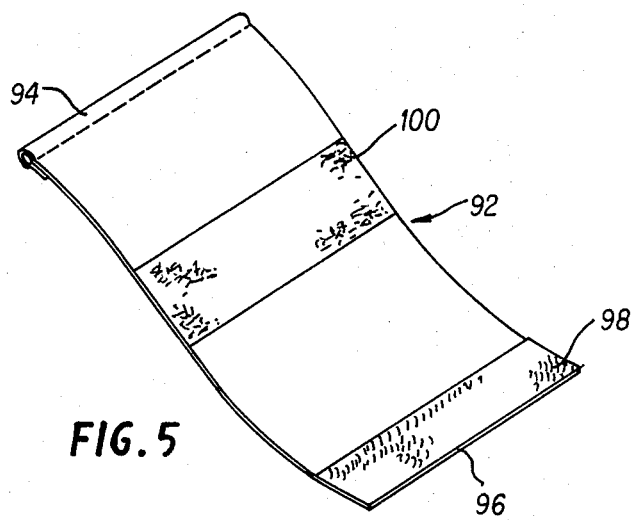
FIG. 5 is a cuff designed for attachment to the wire assembly shown in FIG. 4.

Attachment of cuff 92, provided with velcro hooks section 98 and a velcro loop section 100 as shown in FIG. 5, to the wire assemblies shown in FIG. 4 may then be conducted in the following manner:

Loop end section 94 of cuff 92 is put on wire portion 80 via break 87 with the velcro hooks section 98 and velcro loop section 100 facing outward. Edge 96 is taken over the limb and fed through and under wire portion 83 of wire assembly 62, and then put back on itself whereby velcro hooks 98 adhere to velcro loops 100. This secures one of the four cuffs needed to fix the splint assembly to a limp about a joint. A cuff is attached to wire sections 84 and 86 in a similar manner. The same procedure is used to attach cuffs or straps to the wire sections 81–82 and wire sections 85–87.

Where but a single assembly of an upper and lower strut is to be used the respective cuffs and straps are provided near their ends with suitable securing means such as velcro hooks and loops. It should be understood that while the securing means are shown to be velcro closures other alternative closures, such as snaps and the like can be provided the staps and cuffs.

Figure 8:
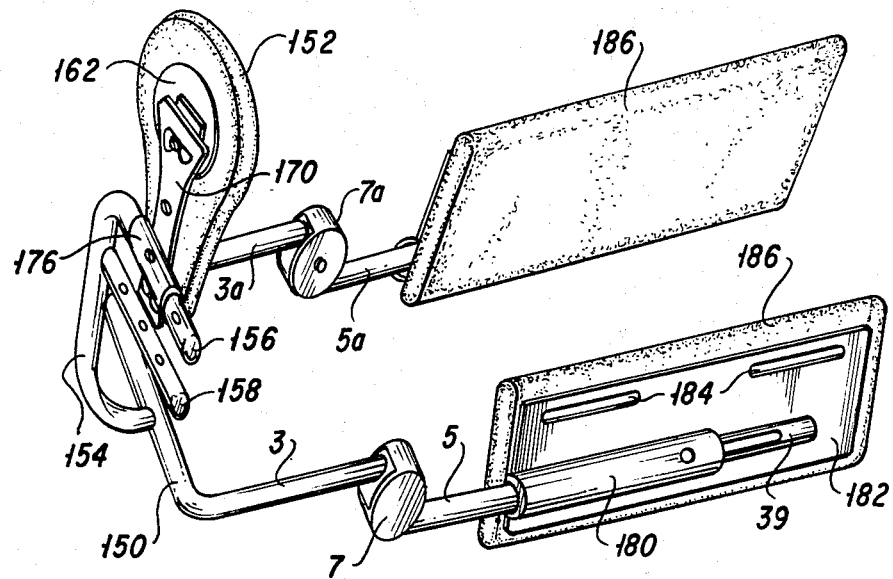
FIG. 8 is a plan view of the splint device including the means for adjusting the splint assembly to the palm.
Figure 9:
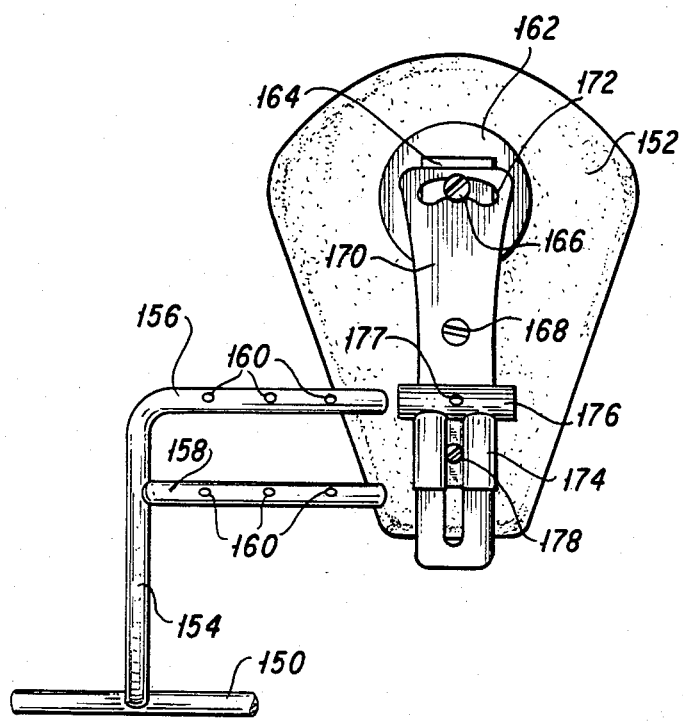
FIG. 9 is a partial front view of the device shown in FIG. 8 with the palmer pressure pad about to be mounted onto a lateral adjusting bar.

The means for adjusting the splint assembly to the palm is shown in FIG. 8 and FIG. 9. Referring to these figures, a member 150 interconnects distal or upper members 3 and 3a. A palmer pressure pad 152, for example, of high density polyurethane is attached to member 150 via a member 154 which is integral with or fixed to interconnecting members 150. The member 154 containing one or more lateral adjusting bars 156 and 158 are each provided with thread holes 160. In the single strut embodiment of the invention, members 150 and 154 connect struct 3 to pad 152.

The palmer pressure pad 152 has attached to one surface a circular plate 162 on which is positioned intermediate fixing plate 164 for receipt of screw members 166 and 168. On top of intermediate plate 164 is positioned a base plate 170 which contains at its upper end an acuate slot 172 through which screw member 166 protrudes and about which the plate 170 rotates. Slidably mounted on base plate 170 is a means indicated generally as 174 which contains a cylindrical sleeve 176 for receipt of any one of the vertical adjusting bars. A port 177 is provided cylindrical sleeve 176 to receive a mounting screw (not shown) that passes through port 177 and a selected coinciding threaded hole 160. The slidably mounted means 174 is slotted to adjust the height of the pad and fixed at the desired height by means of screw means 178.

Proximal strut members 5 and 5a are received by a sleeve 180 mounted on a plate 182. The sleeve 180 and plate 182 are preferably constructed of a plastic material containing slots 184 through which are attached the means for securing the assembly to the forearm. Attached to the opposite sides of the plate 182 are comfort pads 186, preferably of foamed plastic.

The unique characteristics of the adjustable spring-loaded mechanism of the present invention is that it allows for adjustment of quantifiable force on an extremity acting across the body joint from 0 foot poundage up to maximum foot poundage at various body joint ranges.

As an example, in a patient having a wrist flexion contracture, one may want to apply the splint to the wrist and build in a tension of 1 foot pound of force acting on the palm at 10° wrist extension. As the patient develops greater tolerance to the device, in days to come, greater force can be adjusted in the mechanism by simply adjusting the "Allen" wrench 32 and causing greater compression to the spring in the strut. This will exert a greater compression to the spring in the strut. This will exert a greater force toward extending the joint which will ultimately serve a more beneficial purpose in accomplishing reduction of the wrist flexion contracture. In addition, the invention permits the interchangability of springs bearing force-exerting capabilities so as to allow for varying the degrees of tension exerted by the spring mechanism depending upon the particular use to which the device is applied.

The palm pressure pad and the means for adjusting same insures proper location of the pad to achieve the optional combination of patient comfort and mechanical leverage.

Once the beginning tension and duration of splint application is determined, progression of the tension and duration can be accomplished by simple adjustment of the head screw 27 and increasing time, respectively.

A unique feature of this device in the present application to the wrist, and to any body joint, is the ability of this device to alow graduated, quantified, adjustable tension with the ability to relax the stretch across the joint by flexing the wrist from the limitation of extension. This will allow the tissue being stretched to have a rest period while not disturbing the adjustment of the spring tension and without having to remove the splint. In order to relieve the pressure on the contractured tissues, one merely has to overcome, by any means, the tension in the splint and flex the joint to a comfortable posture. Once a short rest is achieved, the splint may again exert its tension against the contractured tissue to help accomplish a greater degree of extension in the joint.

While the features of this invention have been disclosed with reference to the specific embodiments described therein, it is to be understood that various modifications may be made in the construction without departing from the scope of the invention as defined in the appended claims.

It is claimed:

1. An adjustable splint assembly comprising a lower strut and an upper strut pivotably connected to said lower strut, one of said struts having at one end a pivotably mounted head portion defining a cam surface, an adjustable biasing means mounted within the other strut and biased into engagement with said cam surface for applying a quantifiable force tending to align or approximate said upper and lower struts, a palmer pressure pad, means attached to said palmer pressure pad providing both rotational and vertical adjustment of said palmer pressure pad and means connecting the palmer pressure pad to the end of the lower distal strut, said connecting means containing at least one lateral adjusting bar for medial and lateral adjustment of said palmer pressure pad and means for securing said splint assembly to the forearm.

2. An adjustable splint assembly according to claim 1 wherein the means attached to said palmer pressure pad therof comprises a base plate having an arcuate slot, a member fixed to said pad and projecting through said slot about which the pad rotates and a means slidably mounted thereto for vertical adjustment of said pad, said slidably mounted means containing means for receiving said bar for medial and lateral adjustment of said pad.

3. An adjustable splint assembly according to claim 1 wherein the adjustable biasing means is an adjustable spring means.

4. An adjustable splint assembly according to claim 2 wherein the adjustable spring means comprises a spring, a nose element connected to one end of said spring, and adjustable screw means engageable with the other end of said spring.

5. An adjustable splint assembly according to claim 4 wherein the adjustable screw means comprises a spring-abutting member, a screw member threadly engaged in a threaded member fixed to said strut, one end said screw member having a rotatable head and the other end of said screw member being engageable with said spring-abutting member.

6. An adjustable splint assembly according to claim 5 wherein the head is a socket.

7. An adjustable splint assembly according to claim 5 wherein the spring-abutting member is provided with an indicator marking.

8. An adjustable splint assembly according to claim 7 wherein the strut in which the adjustable spring means is mounted is hollow.

9. An adjustable splint assembly according to claim 8 wherein the hollow strut contains a slot having a scale along its length through which the screw member and indicator marking are visible, provided with a scale for setting the force to be applied.

10. An adjustable spring-loaded splint comprising a pair of lower struts and a pair of upper struts, each member of the pair of lower struts being pivotably connected to a member of the pair of upper struts, said members of each pair being spaced apart a distance to accomodate limb parts distal and proximal to the limb joint, at least one of said struts having at one end a pivotably mounted head portion defining a cam surface, an adjustable spring means, mounted within the strut pivotably connected to said cam surface-containing strut and biased into engagement with said cam surface, for applying a quantifiable force tending to align or approximate the cam surface-containing strut with the adjustable spring means, a palmer pressure pad, means attached to said palmer pressure pad providing both rotational and vertical adjustment of said palmer pressure pad, means interconnecting the ends of the lower or distal struts, means connecting the palmer pressure pad to said interconnecting means, said connecting means containing at least one lateral adjusting bar for medial and lateral adjustment of said palmer pressure pad, and means provided said pair and of lower struts for securely holding therebetween the forearm.

11. An adjustable spring-loaded splint assembly according to claim 10 wherein the adjustable spring means comprises a spring, a nose element connected to one end of said spring, an adjustable screw means engageable with the other end of said spring.

12. An adjustable spring-loaded splint assembly according to claim 10 wherein the adjustable screw means comprises a spring-abutting member, a screw member threadly engaged in a threaded member fixed to said strut, one end of said screw member having a rotatable head and the other end of said screw member being engageable with said spring-abutting member.

13. An adjustable spring-loaded splint assembly according to claim 10 wherein the head is a socket.

14. An adjustable spring-loaded splint assembly according to claim 11 wherein the spring-abutting member is provided with an indicator marking.

15. An adjustable spring-loaded splint assembly according to claim 13 wherein the strut in which the spring means is mounted is hollow.

16. An adjustable spring-loaded splint assembly according to claim 15 wherein the hollow strut contains a slot having a scale along its length through which the screw member and indicator-marking are visible, provided with a scale for setting the force to be applied.

* * * * *